United States Patent
Bak et al.

(10) Patent No.: US 9,468,168 B2
(45) Date of Patent: Oct. 18, 2016

(54) *GUZMANIA* 'RETRO'

(71) Applicants: Elly Bak, Assendelft (NL); Nicolaas Steur, Oude Niedorp (NL)

(72) Inventors: Elly Bak, Assendelft (NL); Nicolaas Steur, Oude Niedorp (NL)

(73) Assignee: Corn Bak B.V. (NL)

( * ) Notice: Subject to any disclaimer, the term of this patent is extended or adjusted under 35 U.S.C. 154(b) by 23 days.

(21) Appl. No.: 14/664,013

(22) Filed: Mar. 20, 2015

(65) Prior Publication Data

US 2016/0270314 A1    Sep. 22, 2016

(51) Int. Cl.
*A01H 5/02* (2006.01)
*A01H 1/02* (2006.01)

(52) U.S. Cl.
CPC . *A01H 5/02* (2013.01); *A01H 1/02* (2013.01)

(58) Field of Classification Search
None
See application file for complete search history.

(56) References Cited

U.S. PATENT DOCUMENTS

PP9,670 P  *  10/1996  Hill, Jr. .................... A01H 5/00

* cited by examiner

*Primary Examiner* — David H Kruse
(74) *Attorney, Agent, or Firm* — Cassandra Bright

(57) ABSTRACT

A new and distinct *Guzmania* hybrid named 'RETRO' characterized by solid growth habit; funnel-form rosette plant, measuring about 20-25 cm in height (above the pot when flowering); numerous, green color foliage (measuring about 19 to 28 cm length and about 3 cm in width). Superior floral bract production; bracts are red in color (closest to RHS 44C), singular hear inflorescence, measuring about 9 cm in height and about 13 cm in diameter, and long-lasting habit.

5 Claims, 2 Drawing Sheets
(2 of 2 Drawing Sheet(s) Filed in Color)

GUZMANIA 'RETRO'

FIELD OF THE INVENTION

The present invention relates to a new, distinct and stable hybrid of *Guzmania* hybrid, hereinafter referred to as 'RETRO'. The present invention relates to seeds which are the *Guzmania* hybrid 'RETRO', as well as plants and plant parts produced by these seeds which have all of the morphological and physiological characteristics of the *Guzmania* hybrid 'RETRO'. The present invention also relates to methods for producing these seeds and plants of the *Guzmania* hybrid 'RETRO'. Furthermore, the present invention relates to a method of producing progeny *Guzmania* plants by crossing *Guzmania* 'RETRO', as either the female or seed or male or pollen parent, with another *Guzmania* plant and selecting progeny.

BACKGROUND OF THE INVENTION

The present invention relates to a new, distinct and stable hybrid of *Guzmania* hybrid, and hereinafter referred to by the variety denomination 'RETRO'. The new *Guzmania* 'RETRO' originated from a cross made in a controlled breeding program by the inventors in 2010, and then first flowered in 2013, in Assendelft, the Netherlands. The female or seed parent is the *Guzmania lingulata* inbred line identified by code 100614392 (unpatented). The male or pollen parent is the *Guzmania lingulata* inbred line identified by code 100614254 (unpatented).

*Guzmania* is a member of the Bromeliaceae family. *Guzmania* is predominantly epiphytic with a few terrestrial species and is native to the tropics. For the most part, species vary in diameter from 7 or 8 inches to 3 or 4 feet and have rosette of glossy, smooth-edged leaves.

Floral bracts of *Guzmania* frequently have brilliant colors and may last for many months. The range of colors for *Guzmania* is generally from yellow through orange but may also include flame red and red-purple. White or yellow, tubular, three-petalled flowers may also appear on a stem or within the leaf rosette but are usually short-lived.

*Guzmania* may be advantageously grown as pot plants for greenhouse or home use. Typically, the plants are shaded from direct sunlight. During the spring to autumn period, the central vase-like part of the leaf rosette is normally filled with water.

*Guzmania* is native to tropical America. Leaves of *Guzmania* are usually formed as basal rosettes which are stiff and entire and in several vertical ranks *Guzmania* plants have terminal spikes or panicles which are often bracted with petals united in a tube about as long as the calyx. The ovary is superior and the seeds plumose.

Asexual propagation of *Guzmania* is frequently performed by vegetative means through the use of tissue culture practices. Propagation of *Guzmania* can also be form offshoots which can be detached from the mother plant and growth in an appropriate soil or bark mixture.

Methods for cultivation and crossing of *Guzmania* are well known. For a detailed discussion, reference is made to the following publications, which are incorporated herein by reference: Benzing, David H., *THE BIOLOGY OF THE BROMELIADS*, Mad River Press, Inc., Eureka (1980); Zimmer, Karl, *BROMELIEN*, Veriag, Paul Parey, Berlin (1986); and Rauh, Werner, *BROMELIEN*, Verlag Eugen Ulmer, Stuttgart (1981).

A *Guzmania* inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with their morphological and physiological characteristics.

A need exists for a greater variety of *Guzmania* cultivars with attractive ornamental features. Additionally, a need exists for additional *Guzmania* hybrid cultivars that can be easily propagated by seed. The new *Guzmania* 'RETRO' was developed through a controlled breeding program and exhibits unique, desirable and stable characteristics.

SUMMARY OF THE INVENTION

The present invention provides *Guzmania* plants selections that are solid, small-sized, long-lasting hybrids with superior bract production and red inflorescence that exhibits good keeping quality. The present invention also provides *Guzmania* plants selections with a singular head inflorescence with a unique red color which distinguishes the new cultivar from typical *Guzmania*.

These and other objectives have been achieved in accordance with the present invention which provides 'RETRO' as a new *Guzmania* cultivar that is a product of a planned breeding program conducted by the inventors, Elly Bak and Nico D. M. Steur, in Assendelft, the Netherlands, in 2010. The female or seed parent is the *Guzmania lingulata* inbred line identified by code 100614392 (unpatented). The male or pollen parent is the *Guzmania lingulata* inbred line identified by code 100614254 (unpatented).

Both parental cultivars have a sufficient degree of homozygosity such that the progeny of the cross are genetypically and phenotypically uniform. The new hybrid 'RETRO' therefore can be produced by sexual reproduction by crossing the parental inbred lines identified by the codes 100614392 and 100614254 to produce a population of progeny plants, each of which has the combination of characteristics as herein disclosed for the new hybrid 'RETRO'.

Seeds which are the hybrid 'RETRO' are produced by crossing the parental inbred lines identified by the codes 100614392 and 100614254, and are deposited with the American Type Culture Collection, 10801 University Boulevard, Manassas, Va. 20110-2209 having deposit Designation PTA-122348.

OBJECTS OF THE INVENTION

The present invention related to seeds which produce *Guzmania* hybrid 'RETRO'. The present invention also relates to *Guzmania* plants, and parts thereof, having all physiological and morphological characteristics of *Guzmania* hybrid 'RETRO'. The present invention relates to a plant produced from seeds which are *Guzmania* hybrid 'RETRO'. The present invention also relates to plant parts, such as pollen, seeds or inflorescence produced by *Guzmania* hybrid 'RETRO'.

The present invention relates to a method of producing seed which are *Guzmania* hybrid 'RETRO', by a crossing *Guzmania lingulata* inbred line identified by code 100614392 (unpatented) as the female or seed parent with *Guzmania lingulata* inbred line identified by code 100614254 (unpatented) as the male or pollen parent, harvesting seeds produced from said cross.

The present invention also relates to a method of producing plants having all the physiological and morphological characteristics of the *Guzmania* hybrid 'RETRO' comprising the steps of (a) crossing *Guzmania lingulata* hybrid identified by code 100614392 (unpatented) as a female or seed parent with *Guzmania lingulata* inbred line identified by code 100614392 (unpatented) as the male or pollen parent. (b) harvesting seeds produced from said cross; and (c) producing plants from said harvested seeds.

The present invention also relates to producing progeny plants from the cross of *Guzmania* hybrid 'RETRO', as the female or male parent, with another *Guzmania* plant, and selecting progeny plants from this cross.

BRIEF DESCRIPTION OF THE PHOTOGRAPHS

The patent or application file contains as least one drawing executed in color. Copies of this patent or patent application publication with color drawings will be provided by the Office upon request and payment of the necessary fees.

The accompanying photographs illustrate the overall appearance of the new *Guzmania* hybrid 'RETRO' showing the colors as true as is reasonably possible with colored reproductions of this type. Colors in the photographs may differ slightly from the color values cited in the detailed botanical description which accurately describes the color of 'RETRO'.

DETAILED BOTANICAL DESCRIPTION

Figure 1:
FIG. 1 shows a side view perspective of the primary and top bracts produced by a typical potted, flowering plant of 'RETRO', at 10 months of age from potting size.
Figure 2:
FIG. 2 shows a close-up top view perspective of the inflorescence and top Bracts produced by a typical potted, flowering plant of 'RETRO', at 10 months of age from potting size.

The present invention was created by the inventors, Elly Bak and Nicolaas D. M. Steur in 2010, and flowered for the first time in 2013 in Assendelft, the Netherlands.

This invention is directed to *Guzmania* plant having all the morphological and physiological characteristics of the hybrid 'RETRO' produced from seeds which are the product of the cross of the *Guzmania lingulata* inbred line identified by code 100614392 (unpatented) as the female or seed parent with the *Guzmania lingulata* inbred line identified by code 100614254 (unpatented) as the male or pollen parent. Both parents have a sufficient degree of homozygosity such that the progeny of the cross were, and continue to be, phenotypically uniform. The new hybrid 'RETRO' can therefore be produced by sexual reproduction by crossing of the inbred selections identified by the codes 100614392 and 100614254 to produce a population of progeny plants, each of which has the combination of characteristics herein disclosed for the new hybrid 'RETRO'.

The new hybrid 'RETRO' can also be produced by asexually reproducing progeny from the cross of the parental inbred lines identified by the codes 100614392 and 100614254. Asexual reproduction of the new cultivar by vegetative means by cuttings was first performed in 2013, in Assendelft, the Netherlands. The first 'RETRO' plants propagated through the use of such cuttings flowered in 2014, in Assendelft, the Netherlands, and have demonstrated that the new cultivar reproduces true-to-type and that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be unique characteristics of 'RETRO' which in combination distinguish this *Guzmania* as a new and distinct cultivar:
1. Stemless growth habit;
2. Funnel-form rosette plant, measuring about 20 cm in height (above the Pot when flowering);
3. Numerous, green color foliage (measuring about 25-35 cm in length and about 3 cm in width.
4. Superior floral bract production.
5. Bracts are red in color (closest to RHS 44C)
6. Singular head inflorescence, measuring about 9 cm in height, when Flowering and about 13 cm in diameter.
7. Long-lasting habit.

Of the many commercial cultivars known to the present inventors, the most similar in comparison to the new *Guzmania* hybrid is the *Guzmania* cultivar 'GLOSSITA', U.S. Pat. No. 7,858,857. Plants of the new hybrid 'RETRO' differ from plants of 'GLOSSITA' primarily in color of inflorescence.

'RETRO' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

For example, substantial differences in plant height and diameter, number of leaves, can result depending on the size of the plant at the time that flowering is induced by flowering treatment. Since treatment to induce flowering disrupts normal watering and fertilization regimens. Flowering treatment to relatively smaller plants adversely affects the growth of the plant.

The aforementioned photographs, together with the following observations, measurements and values describe the new *Guzmania* 'RETRO' as grown in a greenhouse in Assendelft, the Netherlands, under conditions which closely approximate those generally used in commercial practice. Plants of 'RETRO' were grown in a greenhouse with day temperatures ranging from 20° C. to 28° C. and night temperatures ranging from 18° C. to 23° C. No artificial lighting or photoperiodic treatments were conducted, but plants of 'RETRO' are forced into flowering. The following fertilizer is added when growing plants of 'RETRO': 1 part nitrogen, 0.6 parts phosphor, 2 parts Kalium and 0.1 parts of magnesium.

Color references are made to the Royal Horticultural Society Colour Chart (RHS), 2001 edition, except where general colors of ordinary significance are used. Color values were taken under daylight conditions in a greenhouse in Assendelft, the Netherlands. The age of the plants of 'RETRO' described is about 12 weeks after flowering treatment.

Classification
Botanical: *Guzmania lingulata* minor
Parentage:
Female Parent: *Guzmania lingulata* minor inbred line identified by code 100614392 (unpatented)
Male Parent: *Guzmania lingulata* minor inbred line identified by code 100614254 (unpatented)
Plant:
General Appearance and Form:
Height: About 20-25 cm (when flowering)
Width: About 50 cm Shape: Funnel form rosette
Growth habit: Stemless
Plant Vigor: Good
Flowering Season: A fully grown plant can flower year round, starting 10-12 weeks after induction of natural light or Through flowering treatment.
Cold Tolerance: Frost tender, Temperature below 5° C. may damage Plants.
Fragrance: None
Foliage:
Quantity: About 16 (depending on the size of the plant)
Size of Leaf:
   Length: About 19 cm to 28 cm (when flowering)
   Width: About 3 cm
Overall Shapes: Linear lanceolate
Apex Shape: Acuminate
Base Shape: Strap-like around central axis
Margin: Entire
Texture: Smooth
Orientation: Leaf blades arch continuously from base.
Color: Leaf color can vary somewhat depending on growing conditions.
Immature and Mature:
   Upper surface: green, RHS 137A
   Under surface: green, RHS 137B
Venation: None
Inflorescence
Borne: Erect
Shape: Singular head
Size:
   Length: About 9 cm in height when flowering
   Diameter: About 13 cm
Time of Bloom: A fully grown plant can produce an inflorescence Containing about 30 flowers (depending on the size of the plants), and can bloom the whole year starting about 10-12 weeks after natural induction or through flowering treatment.
Duration of Bloom: Each flower blooms one (1) day and the total Blooming of the whole inflorescence is about 5 weeks.
Petals:
Number: 3 per flower
Length: About 3 cm
Width: About 0.7 cm
Overall Shape: Ligulate
Apex Shape: Obtuse
Base Shape: Fused
Color:
   Upper and under surfaces: Yellow with a white tip, closest To RHS 9A and RHS 115D
Sepals:
   Number: 3 per flower
   Length: About 3 cm
   Width: About 0.3 cm
   Overall Shapes: Ligulate
   Apex Shape: Acute
   Base Shape: Fused
   Color:
      Upper and under surfaces: Translucent
Bracts:
Scape Bracts:
   Quantity: About 8
   Arrangement: Alternate
   Size:
      Length: About 25 cm (lowest) to about 9 cm (scape bracts Positioned just below the primary bracts).
      Width: About 2.5-3 cm
   Overall Shape: Linear lanceolate
   Apex Shape: Acute
   Base Shape: Fused
   Margin: Entire
   Texture: Smooth
   Upper and under surfaces:
   Scape bracts are green, ranges between RHS 145C and 137C with a Slight red color, closest to RHS 48A, changing to red with a little Green, just below the primary bracts.
Primary Bracts:
Quantity: About 12
Arrangement: Alternative
   Size:
      Length: About 9 cm (lowest) to about 4 cm (primary bracts Shorter closer to the top of plant)
      Width: About 1 cm to 3 cm
Overall shape: Recurved and ovate-lanceolate
Apex shape: Acute
Base shape: Fused
Margin: Entire
Texture: Smooth
Color:
   Upper and under surfaces: Red, closest to RHS 44C
   Floral bracts: Disposed with the inflorescence
Reproductive Organs:
Androecium:
Stamen:
   Number: 6 per flower
   Length: About 4.2 cm
   Diameter: About 1 mm
   Color: Cream, too small to distinguish RHS value
Anther:
   Length: About 0.6 cm
   Color: Cream, too small to distinguish RHS value
Pollen:
   Amount: Scare
   Color: White (too small to distinguish RHS value)
Gynoecium:
Pistil:
   Number: 1 per flower
   Length: About 4.3 cm
Stigma:
   Shape: 3-parted
   Width: About 2 mm
   Color: White, too small to distinguish RHS value
Style:
   Length: About 4.5 cm
   Color: White, too small to distinguish RHS value
Ovary:
   Position: Superior
   Shape: Conical
   Length: About 0.7 cm
   Diameter: About 0.3 cm
   Color: Green-white, closest to RHS 157B
Seeds:
Quantity: About 4000 seeds, found among approximately 20 capsules (depending on the size of the plant). Since the new cultivar is a hybrid, the seeds produced by the plant cannot be used for reproduction.
Size:
   Length: About 4 m
   Diameter: About <1 mm
   Texture: Plumose
Color: Grayed-orange, too small to qualify RHS value
Fruit:
Quantity: About 20 (depending on size of plant)

Type: Casule
Texture: Corded
Color at maturity: Grayed-orange, closest to RHS 165A
Size:
   Length: About 3.5 cm
   Diameter: About 0.6 cm
DISEASE/PEST RESISTANCE/SUSCEPTIBILITY: Neither resistance nor susceptibility observed to date.

We claim:

1. A *Guzmania* plant named 'RETRO', representative seed deposited at the American Type Culture Collection (ATCC) having deposit Designation PTA-122348.

2. A *Guzmania* seed that produces the plant of claim 1.

3. Plant parts obtained from the *Guzmania* plant of claim 1.

4. A method of producing *Guzmania* progeny plant comprising the steps of (a) crossing *Guzmania* 'RETRO' produced from seed deposited with American Type Culture Collection (ATCC) Patent Deposit having deposit Designation PTA-122348 as a female or male parent with a second *Guzmania* plant, and (b) selecting progeny.

5. The method according to claim 4, wherein the second *Guzmania* plant is 'RETRO'.

* * * * *